United States Patent [19]

Jones et al.

[11] Patent Number: 5,558,872
[45] Date of Patent: Sep. 24, 1996

[54] GELLED MINERAL OIL SKIN PROTECTANT

[75] Inventors: David P. Jones; William H. Woller; Cynthia W. Jewett, all of San Antonio, Tex.

[73] Assignee: Healthpoint Medical Limited Partnership, Reno, Nev.

[21] Appl. No.: 400,047

[22] Filed: Mar. 7, 1995

[51] Int. Cl.$^6$ ..................................................... A61K 31/74
[52] U.S. Cl. ........................... 424/78.03; 424/59; 424/60; 424/401; 514/786; 514/846; 514/939
[58] Field of Search ................................ 424/401, 78.03, 424/59, 60; 514/939, 846, 785

[56] References Cited

U.S. PATENT DOCUMENTS

| | | | |
|---|---|---|---|
| 3,608,070 | 9/1971 | Nouvel | 424/80 |
| 5,130,121 | 7/1992 | Kopolow et al. | 424/47 |
| 5,162,378 | 11/1992 | Guthauser | 514/785 |
| 5,221,534 | 6/1993 | DesLauriers et al. | 424/78.03 |

OTHER PUBLICATIONS

CasChem, *Wickenol Isononanoates*, Bayonne, New Jersey (date unknown).
Penrecco, geahlene®, (date unknown).

*Primary Examiner*—Thurman K. Page
*Assistant Examiner*—Sharon Howard
*Attorney, Agent, or Firm*—Zarley, McKee, Thomte, Voorhees, & Sease

[57] ABSTRACT

A clear, gelled mineral oil based skin protectant especially adapted for irritated skin is provided. The product is clear so the underlying compromised skin can be seen, does not have the normal high drag of petrolatum based products and does not dry out. It contains a mineral oil gel blend which is a hydrocarbon mineral oil blended with di- and tri-block copolymers of hydrogenated butylene/ethylene/styrene copolymer and hydrogenated ethylene/propylene/styrene copolymer.

10 Claims, No Drawings

GELLED MINERAL OIL SKIN PROTECTANT

BACKGROUND OF THE INVENTION

This invention relates to a skin protectant, usually for use after skin cleansing. It is a protectant that is especially designed for irritated and compromised skin of the type often accompanying chronic incontinence.

Incontinence, as those involved with hospital health care readily know, often drastically irritates the skin, even causing its surface to be severely compromised. This can and often does cause discomfort and pain to the patient. It is therefore necessary to have effective skin protectants that will protect the compromised skin from the irritation of feces and urine and also be removable by washing.

Many of the protectants that are now used contain a zinc oxide pigment in order to enhance wound healing. Zinc oxide, however, is not particularly liked by hospital care administrators since it masks the underlying wound, making it unavailable for view.

For use with patients associated with chronic diarrhea, enzymatic drainage, or particularly incontinence, a skin protectant needs to be one which provides a good moisture barrier, effectively protects against the irritation caused by feces and urine, and one which is clear for easy observation of the underlying wound. It should also be one which will not dry out.

Basically in providing skin care protectants for incontinence, the nurse applicator has a choice between oil based products and non oil based products. To a certain extent, the choice between those is a matter of preference. Thus, there are some care administrators that will only use oil based products and others that will only use products which avoid an oil base. There is, therefore, a continuing need for effective products of both types.

Turning to the more traditional oil based products, those usually contain petrolatum, or in other words, Vaseline®. While Vaseline has been used as a skin protectant for many years, when it comes to compromised skin particularly of the type associated with incontinence, Vaseline based skin protectants have their problems. In the first instance, they are not clear, and as a result the underlying wound cannot easily be seen. This often is disliked by nurse applicators who cannot accurately assess the underlying wound without clear visibility through the skin care product. Secondly, petrolatum or Vaseline based products have a high degree of drag and therefore hurt both upon application and in removal during cleansing. If the skin is ulcerated in any way, the adhesive or sticky nature of Vaseline may in fact cause damage to the skin both during application and removal.

It therefore can be seen that there is a continuing need for an oil based product which is clear so the underlying wound can be easily seen, which has the correct amount of product drag for use with irritated and compromised skin, and which will not dry out. Ideally the product should have an oily feel as well, but not be unduly greasy. In other words, an oily feel is preferred by some, but too much gives an adverse impression of grease which nurse applicators do not like.

The primary objective of the present invention is to overcome the disadvantages earlier mentioned for traditional oil based skin protectants of the type especially designed for use with irritated skin normally associated with chronic diarrhea, enzymatic drainage or incontinence.

It is a further objective of the present invention to provide a skin protectant which is clear for easy viewing of the underlying wound.

Yet another objective of the present invention is to provide an oil based skin protectant which has the correct drag for use with irritated skin normally associated with incontinence.

A still further objective of the present invention is to provide a skin protectant which has the advantage of oil based skin protectants but which does not use petrolatum, and yet which is stable, easy to formulate, and suitable for use in tube dispensers.

Another objective of the present invention is to provide an anhydrous, crystal clear oil based skin protectant which does not dry out.

The method and manner of accomplishing each of the above objectives as well as others will become apparent from the detailed description of the invention which follows.

SUMMARY OF THE INVENTION

A clear gelled mineral oil based skin protectant, especially adapted for irritated skin is provided. The product is clear so the underlying compromised skin can be seen, does not have the normal high drag associated with petrolatum based products. It contains a mineral oil gel which is a hydrocarbon mineral oil blended with di- and tri-block copolymers of hydrogenated butylene/ethylene/styrene copolymer and hydrogenated ethylene/propylene/styrene copolymer.

The product also contains a compatible modifier to improve feel and make the product less oily, more elegant in feel, and have less drag.

Finally, the product may contain a silicone to provide waterproofing and increased resistance to compromise from feces and urine.

DETAILED DESCRIPTION OF THE INVENTION

A major ingredient for use in the skin protectant of the present invention is a gelled mineral oil product. In particular, the product is formed from certain blends of di- and tri-block copolymers which have advantageous properties. The di- and tri-block copolymers preferably are based on thermoplastic rubbers such as styrene-rubber block copolymers. A suitable gelled mineral oil commercially available that can be used in the composition of the present invention is sold by Penreco Division of Pennzoil products under the trademark Geahlene®. It is a clear, hydrophobic material that Penreco described in their product bulletin as a unique delivery system for topical applications. There is no suggestion in the Penreco product bulletin that such a product could be used in a skin care product especially designed for use with incontinent patients.

The ideal gelled mineral oil product of the present invention is one having a viscosity at 25° C. of from 20,000 cPs to 100,000 cPs. The amount on a weight percent of the total product useful in the present composition generally can range from about 50% to about 99% of gelled mineral oil, and more typically from about 60% to 90% of gelled mineral oil and most preferably around 75%–85% gelled mineral oil. Unless otherwise specified, the percentages given here are all on a weight basis.

Basically, the components of the blend in the gelled mineral oil as used herein are generically described in U.S. Pat. No. 5,221,534 issued Jun. 22, 1993, which is incorporated herein by reference. There the blend of the mineral oil gel is described as being formed by blending these described polymers and, for example, white mineral oil and heating to 50° C. to 90° C. to dissolve the polymer in the oil, while mixing. On cooling, the gel forms. The product is white mineral oil combined with hydrogenated butylene/ethylene/styrene copolymer and hydrogenated ethylene/propylene/styrene copolymer. The amount of mineral oil in the gelled mineral oil blend on a weight basis for this portion only is generally from about 80–99 weight percent of a hydrocarbon oil such as white oil and from about 1 percent to 20 weight percent of a blend of the two different polymer members as above described. The two different polymer members can be commercially available thermoplastic rubber type polymers sold under the trademark Kraton® by Shell Chemical Company. The Kraton® rubber polymers are described as elastomers which have an unusual combination of high strength and low viscosity and a unique molecular structure of linear di-block, tri-block and radial polymers. Each molecule of the Kraton® rubber is said to consist of block segments of styrene monomer units and rubber monomer units. Each block segment may consist of 100 monomer units or more. The most common structure is the linear ABA block type; styrene-butadiene-styrene (SBS) and styrene-isoprene-styrene (SIS), the Kraton® D rubber series. A second generation polymer of this series is the Kraton® G series which are styrene-ethylene-butylene-styrene type (S-EB-S) polymers. Di-block polymers include the ABA type and the SB, styrene-ethylenepropylene (S-EP) and (S-EB). The ABA structure of the Kraton® rubber molecule has polystyrene endblocks and elastomeric midblocks. This series of polymers is sold commercially and indicated as being major compounding ingredients or additives in adhesives, sealants and coatings, asphalt modification for roads and roofing, polymer modification, thermoset modification, and oil modification including use as viscosity index improvers, greases and gels. The Kraton® G rubbers are indicated as being compatible with paraffinic and naphthionic oils and the triblock copolymers are reported as taking up more than 20 times their weight in oil to make a product which can vary in consistency from a "Jello" to a strong elastic rubbery material depending on the grade and concentration of the rubber. The gels are indicated as being used for applications as varied as cable filling or flooding compounds, toys and even strippable sealants and coatings. Certain grades of the Kraton® D series are also indicated as being useful as viscosity modifiers for formulating multi-grade motor oils.

Published International Patent Application No. W88-00603, published Jan. 28, 1988, by Francis et al also describes block copolymers which can be used as one or more components in the present invention. These block copolymers are described as gels or gelloid liquid extended polymer compositions which can comprise an intimate mixture of a block copolymer containing relatively hard blocks and relatively elastomeric blocks, the additional polymer or copolymer material having at least partial compatibility with and a higher glass transition softening or melting temperature than the hard blocks of the block copolymer, and at least 500 parts by weight of extender liquid per 100 parts of the block copolymer, the liquid being present to extend and soften the elastomeric blocks of the block copolymer. The extender liquid can be a hydrocarbon oil and/or a synthetic oil. The gels or gelloid compositions are of the type which can be used in the compositions of the present invention and the entire disclosure of this published application is incorporated herewith.

The Francis et al published International Patent Application also refers to Published European Patent Application No. 224389 of Garmarra et al, published Jun. 3, 1987. This European patent application discloses styrene-diene block copolymer compositions and in particular discloses a mixture of triblock copolymers and a hydrocarbon oil wherein the mixture of triblock copolymers comprises a triblock polymer having (a) styrene to ethylene-butylene ratio of 14 to 30 styrene blocks to 70 to 86 ethylene-butylene blocks, and (b) ethylene-butylene ratio of 31 to 35 styrene blocks to 65 to 69 ethylene-butylene blocks, and wherein the ratio of copolymer A to copolymer B is from about 15 to 85 to about 85 to 15. These compositions are said to be particularly useful as sealing materials. Block copolymers of the type described in this published European application may also be used in the compositions of the invention and the disclosure of European Patent Application No. 224389 is incorporated herein by reference.

A second major component of the skin care protectant of the present invention is a drag modifier or emollient compatible with the gelled mineral oil. Suitable ones are fatty acid ester emollients with the most preferred being isononyl isononanoate available from CASChem, Inc., Bayonne, N.J. as Wickenol 151. The amount of the esterified emollient modifier compatible with the gelled mineral oil can vary from about 1% to about 30% by weight of the total composition, more typically from about 10% to 25%, and most preferably about 20%. While the description herein has been given with a preferred ester modifier, others falling within the general class of fatty acid ester emollients may as well be used, i.e. isopropyl myristate, isopropyl polmitate, butyl stearate. The importance of the ester modifiers is to provide a skin protectant having the correct drag/resistance for a use for compromised skin such as that caused by incontinence. The proper amount will provide the product with a velvety, non greasy feel perceived by nurse applicators and patient as desirable and yet not cause the product to run.

The balance of the system can be minors and can vary, but generally suitable minors would include agents to provide an increased level of waterproofing. Suitable ingredients that may do this are commercially available silicones (dimethicone) at a weight level of from about 1.0% to about 5% by weight.

Non-volatile polyalkylsiloxanes include, for example, polydimethylsiloxanes (Dimethicone) with viscosities ranging from about 5–1000 centistokes (cs) at 25° C. These siloxanes are available, for example, from the General Electric Company as the VISCASIL series and from Dow Corning as the Dow Corning 200 and 225 products. Preferably, the viscosity of these siloxanes selected have a viscosity of about 10 to about 500 cs, and most preferably, a viscosity of up to about 350 cs.

Suitable non-volatile polyalkylaryl siloxanes include, for example, polymethylphenyl siloxanes having viscosities of about 15 to 65 cs at 25° C. These siloxanes are available, for example, from the General Electric as SF 1075 methylphenyl fluid or from Dow Corning as 556 Cosmetic Grade Fluid. Additionally, poly(dimethylsiloxane) (diphenylsiloxane) copolymers having a viscosity in the range of about 10 to 100,000 cs at 25° C. are useful.

The following example is offered to further illustrate but not limit the process and product of the present invention.

EXAMPLE (formulation)

| Component | % W/W |
|---|---|
| Geahlene ® | 79% |
| Isononyl isononanoate | 20% |
| Dimethicone | 1.00% |

The above composition was blended and mixed at room temperature, examined and found to be non irritating, non greasy in feel, substantially waterproof, clear so that underlying skin could be easily seen, and was found by applicators to be elegant, in that it could be put on without tearing the underlying skin and washed off without tearing the underlying skin. It also was found easy to package in tube dispensers.

This gel skin protectant which was especially formulated for incontinent care was then tested in medical centers and in home health care settings with incontinent patients. The product was subjectively evaluated at four different health care facilities with the following overall results.

| Parameter Evaluated | Score* | Number** |
|---|---|---|
| Effectiveness in Protecting from Urine | 2.0 | 4 |
| Effectiveness in Protection from Feces | 2.0 | 4 |
| Ease of Application | 2.5 | 4 |
| Ease of Removal | 2.4 | 4 |
| Fragrance | 1.8 | 4 |
| Reports of irritation | 2.0 | 2 |

*Average of all recorded observations where: 1.0 = Worse; 2.0 = Same; and 3.0 = Better compared to products currently in use.
**Total number of facilities reporting observations in parameter category.

From the above data it can be seen that the product was well accepted by nurse applicators. It provided suitable protection against feces and urine, it did not develop any irritation or breakdown of tissues, and nurse applicators noted its ease of application relative to other available products.

It therefore can be seen that the invention accomplishes all of its stated objectives.

What is claimed is:

1. A smooth, greaseless gelled skin protectant for incontinence, comprising:
   (a) from about 50% to about 99% of a gelled mineral oil, said gelled mineral oil comprising a blend of from about 80% to about 99% by Weight hydrocarbon oil and from about 1% to about 20% by weight of hydrogenated butylene/ethylene/styrene copolymer and hydrogenated ethylene/propylene/styrene copolymer;
   (b) from about 2% to about 40% of a fatty acid ester modifier; and
   (c) from about 1% to about 30% by weight of a silicone agent.

2. The product of claim 1 wherein the amount of gelled mineral oil is from about 60% to about 90% by weight of the product.

3. The product of claim 1 wherein the amount of gelled mineral oil is from about 75% to about 85% by weight of the product.

4. The product of claim 1 wherein the amount of fatty acid ester modifier is from about 1% to about 30% by weight of the product.

5. The product of claim 1 wherein the amount of fatty acid ester modifier is from about 10% to about 20% by weight of the product.

6. The product of claim 1 wherein the amount of fatty acid ester modifier is about 20% by weight of the product.

7. The product of claim 4 wherein the fatty acid ester modifier is selected from the group consisting of isopropyl myristate, isopropyl palmitate and butyl stearate.

8. The product of claim 4 wherein the silicone is dimethicone.

9. The product of claim 8 wherein the dimethicone is present at from about 1% to about 5% by weight of the product.

10. The product of claim 1 wherein the fatty acid ester modifier is isononyl isononanoate.

* * * * *